United States Patent [19]

Lidor et al.

[11] Patent Number: 5,302,741
[45] Date of Patent: Apr. 12, 1994

[54] OPTICAL RESOLUTION OF THREO-2HYDROXY-3-(2-AMINOPHENYL-THIO)-3-(4-METHOXYPHENYL)-PROPIONIC ACID

[75] Inventors: Ramy Lidor; Claude Singer, both of Kfar Saba, Israel

[73] Assignee: Teva Pharmaceutical Industries Ltd., Jerusalem, Israel

[21] Appl. No.: 90,602

[22] Filed: Jul. 12, 1993

[30] Foreign Application Priority Data

Jul. 21, 1992 [IL]  Israel ..................................... 102592

[51] Int. Cl.$^5$ ...................... C07C 319/28; C07B 57/00
[52] U.S. Cl. .......................................... 560/7; 560/17; 562/401; 562/402; 562/431
[58] Field of Search ........................ 562/401, 402, 431; 560/17, 7

[56] References Cited

U.S. PATENT DOCUMENTS

| | | | |
|---|---|---|---|
| 4,552,695 | 11/1985 | Igarashi et al. | 560/17 X |
| 5,008,411 | 4/1991 | Coffen et al. | 560/17 X |
| 5,097,059 | 3/1992 | Giordano et al. | 562/431 X |
| 5,183,922 | 2/1993 | Rizzi et al. | 562/431 X |

FOREIGN PATENT DOCUMENTS

| | | |
|---|---|---|
| 0098892A1 | 7/1982 | European Pat. Off. . |
| 0353538A3 | 7/1989 | European Pat. Off. . |
| 53018038 | 6/1978 | Japan . |
| 59110685 | 10/1984 | Japan . |
| 61207371 | 9/1986 | Japan . |
| 61260044 | 4/1987 | Japan . |

OTHER PUBLICATIONS

Jacques, Jean et al., "Enantiomers, Racemates and Resolutions", 1981, John Wiley & Sons, New York, Brisbane, Chickester, Toranto, pp. 307-312.

Primary Examiner—Arthur C. Prescott
Attorney, Agent, or Firm—Kenyon & Kenyon

[57] ABSTRACT

D(+)-threo-2-hydroxy-3-(2-aminophenylthio)-3-(4-methoxyphenyl)propionic acid, an important intermediate in the synthesis of diltiazem hydrochloride, is obtained in better yields and high optical purity by a novel resolution process comprising the reaction of 2 moles of the (±) racemic acid with 1 mole of quinine and 1 mole of a base in a suitable polar solvent system to form a salt of the D(+) acid and quinine which precipitates; separating said salt and decomposing it with a strong base.

15 Claims, No Drawings

OPTICAL RESOLUTION OF THREO-2HYDROXY-3-(2-AMINOPHENYLTHIO)-3-(4-METHOXYPHENYL)-PROPIONIC ACID

FIELD OF THE INVENTION

The present invention relates to a novel process for the optical resolution of (±)-threo-2-hydroxy-3-(2-aminophenylthio)-3-(4-methoxyphenyl) propionic acid (hereinafter "threo-propionic acid"), an important intermediate in the synthesis of diltiazem hydrochloride.

(±)-Threo-propionic acid has the formula (II)

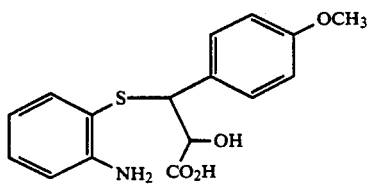

BACKGROUND OF THE INVENTION

Diltiazem, a well known drug with calcium antagonist activity has the formula (I)

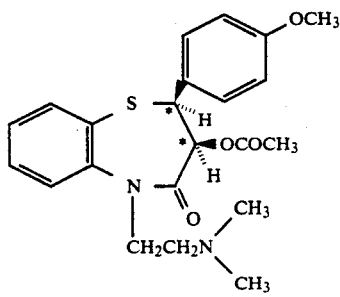

As seen in formula (I), Dilitiazem has two asymmetric carbon atoms (marked with (*)), the configuration of Dilitiazem at its two asymmetric carbons being (2S, 3S).

Numerous methods are known for the synthesis of Dilitiazem from the intermediate threo-propionic acid, and particularly from the optical isomer D(+)-threo-propionic acid.

Several methods have been proposed for the optical resolution of (±) threo-propionic acid (II). Thus, U.S. Pat. No. 4,416,819, JP 103,356 and EP 381,570 describe the use of D(+)-phenylethylamine as the resolving agent for (±)-threopropionic acid.

Other optically active amines such as tolylethylamine (JP 097,606), R(+)-naphtylethylamine (JP 61,207,371) or threo-1-(4-X-phenyl)-2-amino-1,3-propanediol (EP 89,113,135) were also used for the same purpose, while in accordance with JP 8,822,556, IT 023,769 and WO 9100270 L-lysine or phenyl-glycine amide were used instead of the optically active amines as resolving agents.

JP 8,910,617 describes the resolution (±) of erythro-propionic acid by selective hydrolysis of its methyl ester. In this procedure, purification of the separated isomer is necessary, resulting in a reduced yield.

None of the above methods have been found satisfactory, because of low yields, difficult reaction conditions and/or poor recovery of the expensive catalyst or resolving agent.

OBJECT OF THE INVENTION

It is the object of the present invention to provide an improved process for the resolution of (±) threo-propionic acid which process would be free of all the above mentioned shortcomings of the prior art process.

SUMMARY OF THE INVENTION

The present invention thus provides a process for the optical resolution of racemic (±)-threo-2-hydroxy-3-(2-aminophenylthio)-3-(4-methoxyphenyl)propionic acid (A) which comprises reacting two mole equivalents of (A) with one mole equivalent of quinine (B) and with one mole equivalent of a first base in a first polar solvent system, at a temperature from about 20° C. to the reflux temperature of the solvent, to form a precipitate consisting of the quinine salt of D(+) (A) separating the precipitated quinine salt of D(+)-(A) and treating the salt with a strong second base in a second solvent system to yield the corresponding carboxylate salt of the D(+) isomer of (A) with said second base, substantially in optically pure form and quinine in free base form and, if desired, converting said carboxylate salt of D(+)-(A) to the free acid D(+)-(A) by known means.

The novel process of the invention leads to higher yields of the product. The resolving agent used in the process is quinine which can be generated in situ from a suitable organic or inorganic acid addition salt of quinine by reaction with a strong base. This novel resolving agent forms a salt with the D(+)-isomer of threo-propionic acid which is highly insoluble in the specific solvent system used, whereas the quinine salt of L-(−)-threo-propionic acid is more soluble in the same solvent system. As a result, the quinine salt of the D(+) isomer is removed from the reaction system by precipitation, while the L(−) isomer of threo-propionic acid remains in the solution as a salt with the first base.

The quinine resolving agent can be recovered quantitatively by known methods after decomposing the D(+)-threo propionic acid quinine salt with a strong base.

DETAILED DESCRIPTION OF THE INVENTION

The optical resolution process provided by this invention is based on the reaction of a mole equivalent of quinine with two mole equivalents of (±)-threo-propionic acid (II) in the presence of one mole equivalent of a first base, in a suitable polar solvent system, whereby a mole equivalent of D(+)-threo-propionic acid-quinine salt (III) results as the main reaction product. Alternatively, one mole equivalent of a suitable organic or inorganic acid addition salt of quinine may be reacted with two mole equivalents of compound II together with two mole equivalents of a first base whereby one mole of the desired salt III results as the main reaction product. Preferred quinine acid addition salts are the hydrochloride and the acetate.

The first base can be selected from any base whose salt with the L(−)-threo-propionic acid (II) is soluble in the first polar solvent or solvent system. Preferred bases are sodium or potassium hydroxide, sodium or potassium carbonate, diethylamine or dibutylamine.

The first polar solvent system is a most important factor for a successful optical resolution. Preferably the first solvent system is an alkanol-water system, such as isopropanol-water, ethanol-water or methanol-water. Other polar solvent systems, such as dimethylformamide, dimethylformamide-acetone, dimethylformamide-alkanol, dimethylformamide-alkanol-water, were also found suitable. Two-phase systems such as a mixture of ethyl acetate-methanol-water can also be employed in the optical resolution process of the invention.

Preferably, the resolution reaction is carried out by adding the resolving agent dissolved in a suitable solvent or in powder form, to the suspension of the (±)-threo-propionic acid in the presence of the first base.

The temperature of the solvent system when the resolving agent is added may vary from room temperature to the reflux temperature of the solvent or solvent system. Preferably the temperature is the reflux temperature of the solvent system. The resolving agent can be added in one lot, but is preferably added portion wise over a period of several hours.

The quinine is displaced from its salt with the D(+)-threo-propionic acid (III) by treatment with a strong base (the second base) in a second solvent system which is suitable for the recovery of quinine free base.

Suitable second solvent systems are e.g., water or 2-phase systems such as water-toluene. Additionally, the solvent system may contain a surfactant such as Triton X-100 or silicone oil.

The preferred strong second bases are NaOH or KOH. However, other strong bases may also be used. The recovery reaction proceeds at temperatures between room temperature and the solvent reflux temperature. The preferred temperature range is 70°–90° C.

The products of the recovery reaction are the optically active base quinine, which can be recycled to a further resolution, and the salt of the D(+)-threo-2-propionic acid with the cation of the second strong base. This salt can be used as such for the synthesis of Diltiazem according to well known methods, such as those described in U.S. Pat. No. 4,416,819.

The invention will be further described in more detail with the aid of the following non-limiting examples.

EXAMPLE 1

31.9 g (0.1M) of (±)-threo-2-hydroxy-3-(2-aminophenylthio)-3-(4-methoxyphenyl)-propionic acid (II) were suspended in 160 ml of a mixture of water-methanol (1:4) and the suspension heated to 40° C. At this temperature 5.3 g (0.05M) of $Na_2CO_3$ were added while stirring and the mixture was heated to reflux. At reflux temperature a solution of 16.2 g (0.05M) of quinine in 160 ml of methanol was added gradually to the reaction mixture during four hours. The obtained suspension was refluxed for a further half hour and cooled to room temperature. The resulting precipitate of D(+)-threo-2-hydroxy-3-(2-aminophenylthio)-3-(4-methoxy-phenyl)-propionic acid quinine salt (III) was filtered, washed three times with methanol and dried m.p. 226°.

Yield—31.2 g (0.0485M) (97%).
Optical assay: 98.5% ($[\alpha]_D$ at 20° C.= +236°).

EXAMPLE 2

31.9 g of (0.1M) (±)-threo-2-hydroxy-3-(2-aminophenylthio)-3-(4-methoxy-phenyl)-propionic acid (II) were suspended in 225 ml of methanol and the suspension heated to 40° C. At this temperature 4 g (0.1M) of NaOH dissolved in 60 ml of water were added under stirring, and the heating was continued until reflux temperature was reached. At reflux temperature a solution of 19.2 g (0.05M) of quinine acetate in 225 ml of methanol was gradually added to the reaction mixture during two hours. The resulting suspension was maintained at reflux for another half hour, and cooled to room temperature. The D(+)-threo-2-hydroxy-3-(2-aminophenylthio)-3-(4-methoxyphenyl) propionic acid quinine salt (III) was filtered, washed three times with methanol and dried.

Yield—28.3 g (0.044M) (88%).
Optical assay: 97% ($[\alpha]_D$ at 20° C.= +233°).

EXAMPLE 3

31.9 g (0.1M) of (±)-threo-2-hydroxy-3-(2-aminophenylthio)-3-(4-methoxyphenyl)-propionic acid (II) were suspended in a mixture of 250 ml of methanol and 60 ml of DMF. At 40° C. 2 g (0.05M) of NaOH were added and the suspension was heated to 60° C. At this temperature a solution of 16.2 g (0.05M) of quinine was added gradually to the reaction mixture during four hours. The suspension was then refluxed for half an hour and cooled to room temperature. The D(+)-Threo-2-hydroxy-3-(2-aminophenylthio)-3-(4-methoxyphenyl)-propionic acid quinine salt (III) was filtered, washed three times with methanol and dried.

Yield—27.3 g (0.042M) (85%).
Optical assay: 97% ($[\alpha]_D$ at 20° C.= +235°).

EXAMPLE 4

31.9 g (0.1M) of (±)-threo-2-hydroxy-3-(2-aminophenylthio)-3-(4-methoxyphenyl)-propionic acid (II) were suspended in a mixture of 430 ml of ethanol and 50 ml of water. At 40° C. 2 g (0.05M) of NaOH were added and the suspension was heated to 60° C. 16.2 g (0.05M) of quinine were added gradually over one hour and the suspension was maintained for another half hour at the reflux temperature and then cooled to room temperature. The D(+)-threo-2-hydroxy-3-(2-aminophenylthio)-3-(4-methoxyphenyl)-propionic acid quinine salt (III) was filtered, washed three times with methanol and dried.

Yield—28.5 g (0.44M) (88.6%).
Optical assay: 97.5% ($[\alpha]_D$ at 20° C.= +234°).

EXAMPLE 5

31.9 g (0.1M) of (±)-threo-2-hydroxy-3-(2-aminophenylthio)-3-(4-methoxy-phenyl)-propionic acid (II) were suspended in a mixture of 80 ml of ethyl acetate and 80 ml of water and heated to 40° C. At this temperature 5.3 g of $Na_2CO_3$ (0.05M) were added while stirring and the mixture was then heated to the reflux temperature. At reflux a solution of 16.2 g (0.05M) of quinine in 160 ml of methanol was added to the reaction mixture during four hours. The obtained suspension was maintained for another half hour at reflux, and cooled to room temperature. The D(+)-threo-2-hydroxy-3-(2-amino-phenylthio)-3-(4-methoxyphenyl)-propionic acid quinine salt (III) was filtered, washed three times with methanol and dried.

Yield—30.2 g (0.047M) (94%).
Optical assay: 97% ($[\alpha]_D$ at 20° C.= +232°).

EXAMPLE 6

Recovery of Quinine 64.3 g (0.1M) of D(+)-threo-2-hydroxy-3-(2-aminophenylthio)-3-(4-methoxy-phenyl)-propionic acid quinine salt (III) were suspended in a 2-phase solvent system consisting of 225 ml of water and 32 ml of toluene. The mixture was heated to 40° C., 6 g (0.15M) of NaOH in 100 ml of water were added, and the reaction mixture was further heated to 75° C. The obtained suspension was maintained for 2 hours at this temperature, cooled to 15° C., filtered and dried.

Yield—31.6 g (0.097M) of quinine (97.5%).

The filtrate containing the Na salt of the D(+)-threo-2-hydroxy-3-(2-aminophenylthio)-3-(4-methoxyphenyl)-propionic acid (IV) which can be used as such in the Diltiazem synthesis.

EXAMPLE 7

Recovery of Quinine

A solution of 8.4 g (0.15M) of KOH in 325 of water containing 0.65 g of the surfactant Triton X-100 was heated to 75° C. and 64.3 g (0.1M) of D(+)-threo-2-hydroxy-3-(2-aminophenylthio)-3-(4-methoxyphenyl)-propionic acid quinine salt (III) was added during half an hour. The obtained suspension was heated to 85° C. and maintained at this temperature for two hours, cooled to 25° C. and filtered, yielding 31.75 of quinine, (0.098M) (98%).

As in Example 6, the filtrate containing the potassium salt of the D(+)-threo-2-hydroxy-3-(2-aminophenylthio)-3-(4-methoxyphenyl)propionic acid (IV) which was further used in the Diltiazem synthesis.

EXAMPLE 8

Recovery of Quinine 64.3 g (0.1M) of D(+)-threo-2-hydroxy-3-(2-aminophenylthio)-3-(4-methoxy-phenyl)-propionic acid quinine salt (III) were suspended in a 2-phase solvent system consisting of 187 ml of water and 187 ml of toluene. The mixture was heated to 40° C., 6.2 g (0.155M) of NaOH were added, and the mixture was then heated to 75° C. After 0.5 hour at this temperature the toluene phase and the water phase were separated at 70° C. The toluene solution was cooled to 10°–15° C. during 2 hours and the quinine which crystallized was then filtered at 15° C.

Yield —31.65 g (0.098M) of quinine, (97.7%).

The aqueous solution contained the Na-salt of D(+)-threo-2-hydroxy-3-(2-aminophenylthio)-3-(4-methoxyphenyl)-propionic acid (IV) and was further used in the Diltiazem synthesis.

EXAMPLE 9

Precipitation of D(+)-threo-2-hydroxy-3-(2-aminophenylthio)-3-(4-methoxyphenyl)propionic acid From the aqueous solution of the Na salt of D(+)-threo-2-hydroxy-3-(2-aminopehnylthio)-3-(4-methoxyphenyl)-propionic acid (IV) obtained in Example 8, the free acid was precipitated as follows:

The aqueous solution of IV (0.1M) (Example 8) was concentrated from 190 ml down to 100 ml, cooled to 50° C. and added gradually to a solution of 4.8 g (0.048M) of $H_2SO_4$ (98%) in 90 ml of water at 50° C. After adding about 50 ml the addition was interrupted for one hour to allow the D(+)-threo-propionic acid crystals to grow. The remainder of the solution of the D(+)-threopropionic acid Na salt was then added during 1.5 hours. The suspension was cooled for two hours at 5° C. and filtered. After drying, 29.3 g (0.092M) of pure D(+)-threopropionic acid, were obtained as a crystalline white power. The optical rotation was the same as reported in EP 98,892.

Yield —92%;

$[\alpha]_D$ at 23° C.=+346°.

We claim:

1. A process for the optical resolution of racemic (±)-threo-2-hydroxy-3-(2-aminophenylthio)-3-(4-methoxyphenyl) propionic acid (A) which comprises:
   reacting two mole equivalents of (A) with one mole equivalent of quinine (B) and with one mole equivalent of a first base in a first polar solvent system, at a temperature from about 20° C. to the reflux temperature of the solvent system, to form the quinine salt of D(+)-(A) which precipitates;
   separating the quinine salt of D(+)-(A);
   treating the said salt with a strong second base in a second solvent system to yield the corresponding carboxylate salt of the D(+) isomer of (A) with said second base, substantially in optically pure form, and quinine in free base form;
   and, if desired, converting said carboxylate salt of D(+) (A) to the free acid D(+) (A) by known means.

2. A process according to claim 1 wherein the quinine (B) is generated in situ by decomposing a quinine addition salt of an organic or inorganic acid by reaction with one mole equivalent of a strong base.

3. A process according to claim 2, wherein the quinine is obtained from quinine hydrochloride or quinine acetate.

4. A process according to claim 1, wherein said first polar solvent system comprises an alkanol-water mixed solvent.

5. A process according to claim 4, wherein said first polar solvent system comprises a methanol-water mixed solvent.

6. A process according to claim 1, wherein said first polar solvent system comprises a dimethylformamide-alkanol mixed solvent.

7. A process according to claim 1, wherein said first polar solvent system comprises a biphasic mixture of ethyl acetate and water.

8. A process according to claim 1, wherein the reaction is carried out at a temperature of from about 40° C. to about the reflux temperature of said first polar solvent system used.

9. A process according to claim 1, wherein said first base is sodium hydroxide, potassium hydroxide, sodium carbonate, potassium carbonate, diethylamine or dibutylamine.

10. A process according to claim 1, wherein said second strong base is sodium hydroxide or potassium hydroxide.

11. A process according to claim 1, wherein said second solvent system is a 2-phase system.

12. A process according to claim 11 wherein said 2-phase solvent system comprises a water-toluene mixture.

13. A process according to claim 1, wherein said second solvent system additionally contains a surface active agent.

14. A process according to claim 13 wherein said surface active agent is silicon oil or triton X-100.

15. D(+)-threo-2-hydroxy-3-(2-aminophenylthio)-3-(4-methoxy-phenyl)-propionic acid quinine salt.

* * * * *